(12) United States Patent
Watson

(10) Patent No.: US 8,545,422 B2
(45) Date of Patent: Oct. 1, 2013

(54) MOLDABLE DECORATIVE MATERIAL FOR SPLINTS OR CASTS

(76) Inventor: Cristina Watson, Chelmsford, MA (US)

( * ) Notice: Subject to any disclaimer, the term of this patent is extended or adjusted under 35 U.S.C. 154(b) by 41 days.

(21) Appl. No.: 13/021,169

(22) Filed: Feb. 4, 2011

(65) Prior Publication Data

US 2012/0203155 A1 Aug. 9, 2012

(51) Int. Cl.
*A61F 5/00* (2006.01)

(52) U.S. Cl.
USPC ........................................ 602/7; 602/5; 602/6

(58) Field of Classification Search
USPC .................... 602/3, 6, 7; D24/171, 189–192; 2/16, 22, 244, 255, 455
See application file for complete search history.

(56) References Cited

U.S. PATENT DOCUMENTS

| | | | |
|---|---|---|---|
| 3,692,023 A * | 9/1972 | Phillips et al. | 602/7 |
| 4,240,415 A | 12/1980 | Wartman | |
| RE30,541 E | 3/1981 | Larson | |
| 4,661,535 A | 4/1987 | Borroff et al. | |
| 5,342,291 A | 8/1994 | Scholz et al. | |
| 5,439,438 A | 8/1995 | Ersfeld et al. | |
| 5,573,501 A | 11/1996 | Ruscito et al. | |
| 5,603,691 A | 2/1997 | Scholz et al. | |
| 6,093,161 A | 7/2000 | Vlaeyen et al. | |
| 6,110,134 A | 8/2000 | Clark, Jr. et al. | |
| 7,089,764 B2 | 8/2006 | Brett | |
| 7,468,047 B2 | 12/2008 | Nieberding | |
| 2002/0069671 A1 | 6/2002 | Richardson | |
| 2005/0101899 A1 | 5/2005 | Wegmann | |
| 2007/0004993 A1 | 1/2007 | Coppens et al. | |
| 2007/0232979 A1 | 10/2007 | Montgomery | |
| 2007/0283597 A1 | 12/2007 | Logan | |
| 2010/0292620 A1 | 11/2010 | Lattimore | |

FOREIGN PATENT DOCUMENTS

| | | |
|---|---|---|
| DE | 4218498 | 8/1993 |
| EP | 358451 | 12/1993 |
| EP | 2233812 A1 | 9/2010 |
| RU | 2127569 C1 | 3/1999 |
| RU | 79759 U1 | 1/2009 |
| UA | 56953 U | 1/2011 |
| WO | WO 97/04936 A1 | 12/1997 |

OTHER PUBLICATIONS

International Search Report and Written Opinion for PCT/US2012/023580, mailed May 11, 2012.
"Fabian Seibert" Suelz Kotlett http://www.suelzkotlett.com/index.php?page=04, retrieved from Internet, Aug. 2010.
"Exciting way to decorate your leg or arm cast" OrthoTape http://orthotape.com/casttoo_cast_tattoo.asp, retrieved from Internet, Aug. 2010.
"What is Shrinkins?" SHRINKins http://shrinkins.com/index.html, retrieved from Internet, Aug. 2010.

* cited by examiner

*Primary Examiner* — Patricia Bianco
*Assistant Examiner* — Keri J Nelson
(74) *Attorney, Agent, or Firm* — Wolf, Greenfield & Sacks, P.C.

(57) ABSTRACT

A moldable decorative splint material includes a heat-moldable sheet of splint material adapted to become sufficiently pliable when heated to a first temperature to allow the sheet to be molded into a splint configuration that conforms to an anatomical body part and to become hard when cooled to a second temperature to retain the splint configuration. The splint material includes a plurality of decorative elements integrated with the sheet of splint material. The decorative elements are to be retained by the sheet of splint material when the sheet is heated to the first temperature, molded into a splint configuration, and cooled to the second temperature.

21 Claims, 10 Drawing Sheets

MOLDABLE DECORATIVE MATERIAL FOR SPLINTS OR CASTS

FIELD OF THE INVENTION

The invention relates generally to splints and casts, and more specifically to a moldable decorative material used to make splints and casts.

BACKGROUND

Casts and splints are applied to patients to stabilize, immobilize and/or provide support to injured body parts. A heat-moldable sheet made of a low temperature thermoplastic may be used to form a splint or cast. Typically, the sheet is placed in heated water to heat the material until the thermoplastic becomes sufficiently pliable to be molded into a splint shape. A medical professional then molds the sheet to the portion of the patient being treated to form the splint or cast. As the material cools, it hardens to form the splint or cast.

SUMMARY

According to one embodiment of the invention, a moldable decorative splint material includes a heat-moldable sheet of splint material adapted to become sufficiently pliable when heated to a first temperature to allow the sheet to be molded into a splint configuration that conforms to an anatomical body part and to become hard when cooled to a second temperature to retain the splint configuration. The splint material includes a plurality of decorative elements integrated with the sheet of splint material. The decorative elements are to be retained by the sheet of splint material when the sheet is heated to the first temperature, molded into a splint configuration, and cooled to the second temperature.

According to another embodiment of the invention, a method of fabricating a moldable decorative splint material includes an act of providing a heat-moldable splint material adapted to become sufficiently pliable when heated to a first temperature to allow the splint material to be molded into a splint configuration that conforms to an anatomical body part and to become hard when cooled to a second temperature to retain the splint configuration. The method further includes an act of integrating a plurality of decorative elements with the splint material, wherein the decorative elements are to be retained by splint material when the splint material is heated to the first temperature, molded into a splint configuration, and cooled to the second temperature.

According to a further embodiment of the invention, a method of applying a splint to a patient includes an act of heating a sheet of splint material to a first temperature at which the splint material becomes sufficiently pliable to allow the sheet to be molded into a splint configuration that conforms to an anatomical body part. The splint material is integrated with a plurality of decorative elements that remain integrated with the splint material during heating. The method also includes molding the sheet of splint material over the anatomical body part and into the splint configuration, and cooling the sheet of splint material until the splint material hardens to retain the splint configuration.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
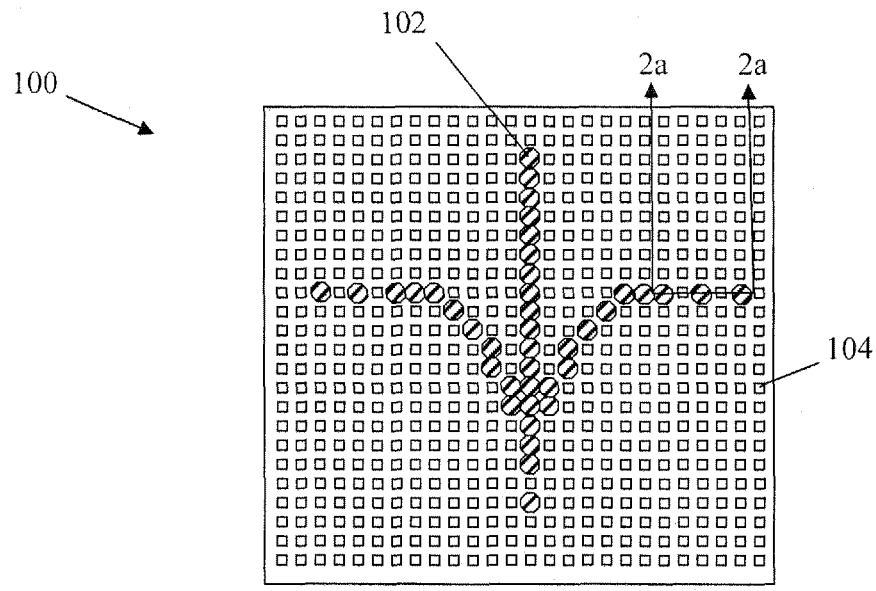
FIG. 1 is a top view of a sheet of splint or cast material including decorative elements according to one embodiment of the invention.

For ease of understanding, and without limiting the scope of the invention, the devices to which this patent is addressed are disclosed below particularly in connection with splint materials and splints. For purposes herein, the term "splint material" means materials configured to be used in a splint, a cast, or other apparatus configured to support, stabilize, and/or immobilize an anatomical body part. Similarly, for purposes herein, the term "splint" means a splint, a cast, or other apparatus configured to support, stabilize, and/or immobilize an anatomical body part.

Splints are typically used when a person has been injured, has had surgery, or requires support, immobilization or stabilization for other medical reasons. Often, the patient may view the splint as unattractive and/or as a visual reminder of his or her injury. In some cases, these concerns may lead a patient to have a negative attitude regarding the splint, resist use of the splint, or perhaps request removal of the splint earlier than medically advisable.

Embodiments disclosed herein provide a visually appealing splint material which may aid in persuading a patient to properly use the splint, and also may improve a patient's outlook regarding their medical condition. Additionally, by providing a variety of decorative splint material options, a patient may be provided with a choice as to the visual appearance of his or her splint, which may allow a patient to express their particular style or color preference, thereby giving their splint a personalized or customized look.

According to some embodiments of the invention, a heat-moldable splint material includes decorative elements, such as rhinestones, which are integrated with the splint or cast material prior to applying the splint to the patient. When the splint material is heated for shaping over a patient's body part, the decorative elements remain integrated with the material. Once the material cools and hardens, a visually attractive splint is formed.

In some embodiments, the decorative elements are embedded in a sheet of splint material. For example, rhinestones (or other decorative elements) may be embedded in the sheet of splint material during manufacture of the sheet. In other embodiments, a previously manufactured sheet of material may be heated to a softened state, and decorative elements may be embedded in the sheet by pressing the decorative elements into the sheet. The sheet may be cooled to a hardened state and stored and/or transported until needed for application to a patient. In still further embodiments, decorative elements may be attached to a sheet of splint material with an attachment element, such as a monofilament line.

By providing a sheet of splint material with previously integrated decorative elements, a patient may have a decorated splint applied without requiring a subsequent step of adding decorative elements to the splint.

A low temperature thermoplastic may be used to form a sheet of splint material. Low temperature thermoplastics can be heated to a temperature at which the thermoplastic softens and becomes sufficiently pliable for molding the material into a desired shape. After cooling for a sufficient amount of time, the material hardens and maintains the desired shape. To soften low temperature thermoplastics, the material is typically heated to at least its melting point temperature using either heated water or heated air.

One example of a low temperature thermoplastic which may be used as splint material is poly epsilon caprolactone, which has a melting point temperature of approximately 62 degrees Celsius. According to some embodiments of the invention, a thermoplastic having a melting point temperature between 50 degrees Celsius and 100 degrees Celsius inclusive may be used as at least a portion of the material for a sheet of splint material. In some embodiments, a low temperature thermoplastic having a melting point temperature between 62 degrees and 75 degrees inclusive may be used. In some embodiments, a low temperature thermoplastic with a melting point temperature of approximately 62 degrees Celsius may be used.

The splint materials to which embodiments disclosed herein apply may be applied to a patient's arm, wrist, ankle, leg, nose or any other body part in need of support, stabilization and/or immobilization. In some embodiments, a sheet of splint material may be trimmed by a medical professional to a suitable size and shape according to the size and shape of the anatomical body part to be treated. In other embodiments, a sheet of splint material may be pre-cut or otherwise pre-shaped for a particular body part before being provided to the medical professional. In still further embodiments, a pre-cut or otherwise pre-shaped sheet may be provided, and the medical professional may perform additionally trimming to customize the sheet before heating.

A sheet of splint material may include decorative elements arranged in a specific design, such as shown in FIG. 1. In one illustrative embodiment shown in FIG. 1, rhinestones 102 are embedded within a low temperature thermoplastic sheet 100. Perforations 104 may be provided in the sheet for breathability of the splint once in place on the patient. The perforations also may facilitate molding of the sheet when shaping the sheet into a splint on the patient. Of course, in some embodiments, a sheet of splint material may be provided without perforations, or the perforations may be provided only in certain sections of the sheet.

Each rhinestone 102 may be positioned over a perforation 104 in the embodiment of FIG. 1. In other embodiments, decorative elements may be positioned off-center from perforations 104, or may be irregularly or randomly positioned relative to perforations 104.

As shown in FIG. 1, some rhinestones 102 may be positioned directly adjacent to one or more rhinestones, while other rhinestones may be separated from their nearest neighbor rhinestones by one or more perforations. In embodiments where a large number of decorative elements are integrated with a sheet, the decorative elements may be positioned to provide bands free of decorative elements to facilitate trimming of the sheet. For example, in some embodiments, patterns of decorative elements may be provided wherein columns of perforations alternate between columns including decorative elements and columns not including decorative elements.

Although the embodiment shown in FIG. 1 has been described as including rhinestones, other types of decorative elements may be used, including beads, gemstones, crystals, jewels, or any other desired decorative elements as would be apparent to one of skill in the art. In some embodiments, combinations of different types of decorative elements may be used on the same sheet.

As shown in FIG. 1, the sheet may have a square shape. However, sheets of other suitable shapes or configurations may be used with embodiments disclosed herein. For example, a trapezoidal shaped sheet (see FIG. 9a), a rectangular shaped sheet, a substantially triangular shaped sheet (see FIG. 9c), a sheet having one or more curved edges (see FIGS. 9b and 9d), or any other suitable sheet shape may be used. In some embodiments, sheets may be pre-cut into shapes which are intended for specific body parts, such as the nose, wrist or ankle.

In one embodiment, the sheet of splint material may be formed with a low temperature thermoplastic, such as 2-Oxepanone, polymer with 1,4-butanediol available under the tradename Aquaplast RT™ Thermoplastic available from WFR/Aquaplast Corporation of Wyckoff, N.J. Synonyms for this material include caprolactone and poly epsilon caprolactone. A sheet of heat-moldable material may be manufactured of poly epsilon caprolactone using plastics extrusion. Crosslinked polymeric components other than a poly epsilon caprolactone may be used in some embodiments.

In some embodiments, sheets may be formed using extrusion compounding of two or more materials, for example, 95% poly epsilon caprolactone and 5% trimethylolpropane trimethacrylate. Other materials may include a mixture of poly epsilon caprolactone and a thermoplastic rubber, such as styrene-butadiene-styrene. Other suitable materials may include poly ethyleneadipate, polyvinyl stearate and cellulose acetate. In still further embodiments, sheets of material made from non-thermoplastic materials may be used. For example, in some embodiments, decorative elements may be joined to fiberglass material with attachment elements.

It is to be understood that the sheet of splint material need not necessarily be provided in a planar shape. For example, in some embodiments, a curved or bent piece of material may be provided and still be considered to be a sheet. With materials which are particularly flexible even below their melting point, a sheet of material may be provided as a roll of material.

Figure 2A:
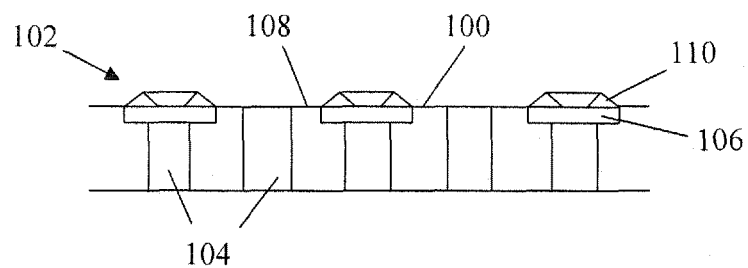
FIG. 2a is a partial cross-sectional view taken along line B-B of FIG. 1.

In one illustrative embodiment, decorative elements may be integrated with a sheet of splint material by embedding the decorative elements in the material of the sheet itself. For example, as shown in FIG. 2a, each rhinestone 102 may be embedded in a sheet 100 so that a base 106 of the rhinestone 102 is held within the material below an upper surface 108 of the sheet 100, while a decorative upper portion 110 of the rhinestone 102 protrudes from the upper surface 108. In other embodiments, the entire rhinestone (or other decorative element) may be embedded in the material so that no part of the rhinestone protrudes above the upper surface 108, that is, the decorative upper portion 110 of the rhinestone is either flush with the upper surface 108 or sunken within the material.

As discussed further above, each rhinestone 102 may be embedded at a location of a perforation 104. In some embodiments, the perforations 104 may be formed after the sheet of material is formed, for example by puncturing the sheet with needles. In such embodiments, the perforations may be formed after the rhinestones 102 are embedded in the sheet 100, and thus while it may appear that the rhinestones 102 cover perforations based on the layout of rhinestones and perforations, the rhinestones may be embedded over a solid section of the sheet 100.

Figure 2B:
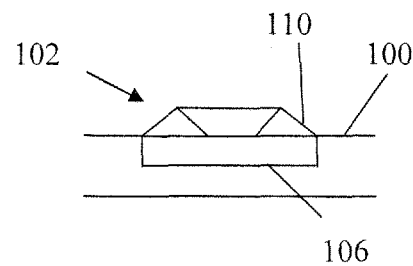
FIG. 2b is cross-sectional view of splint or cast material including a decorative element according to one embodiment of the invention.

In some embodiments, the decorative elements may be embedded substantially into the thickness of the sheet of splint material. For example, as shown in FIG. 2b, the base 106 of the rhinestone 102 may be embedded to a depth which is approximately halfway through the thickness of the sheet 100. In other embodiments, decorative elements may be embedded at any suitable depth as would be apparent to one of ordinary skill in the art.

Decorative elements may be embedded in a sheet of splint material during the process of forming the sheet. For example, a method of manufacturing a sheet of splint material may include a molding process which is used to embed decorative elements. One illustrative embodiment of a mold and a method of manufacturing 400 is described below with reference to FIGS. 3 and 4.

Figure 3:
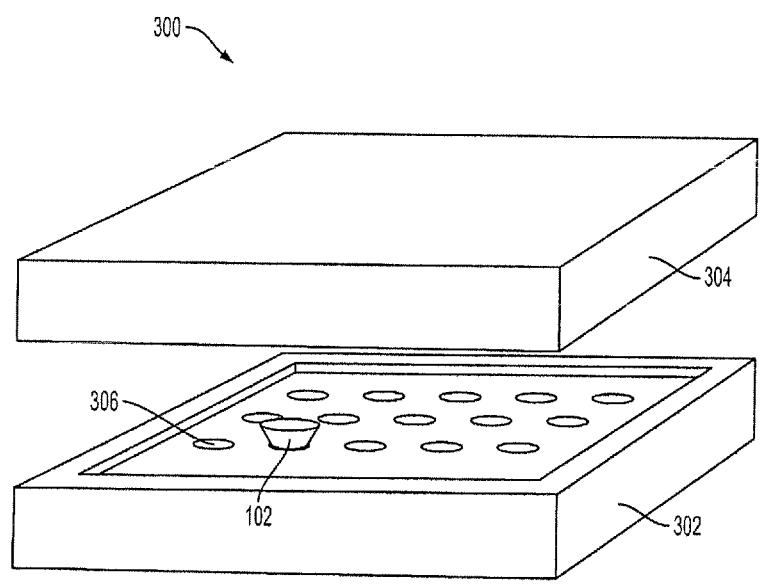
FIG. 3 is a perspective view of a mold for forming a sheet of splint or cast material.
Figure 4:
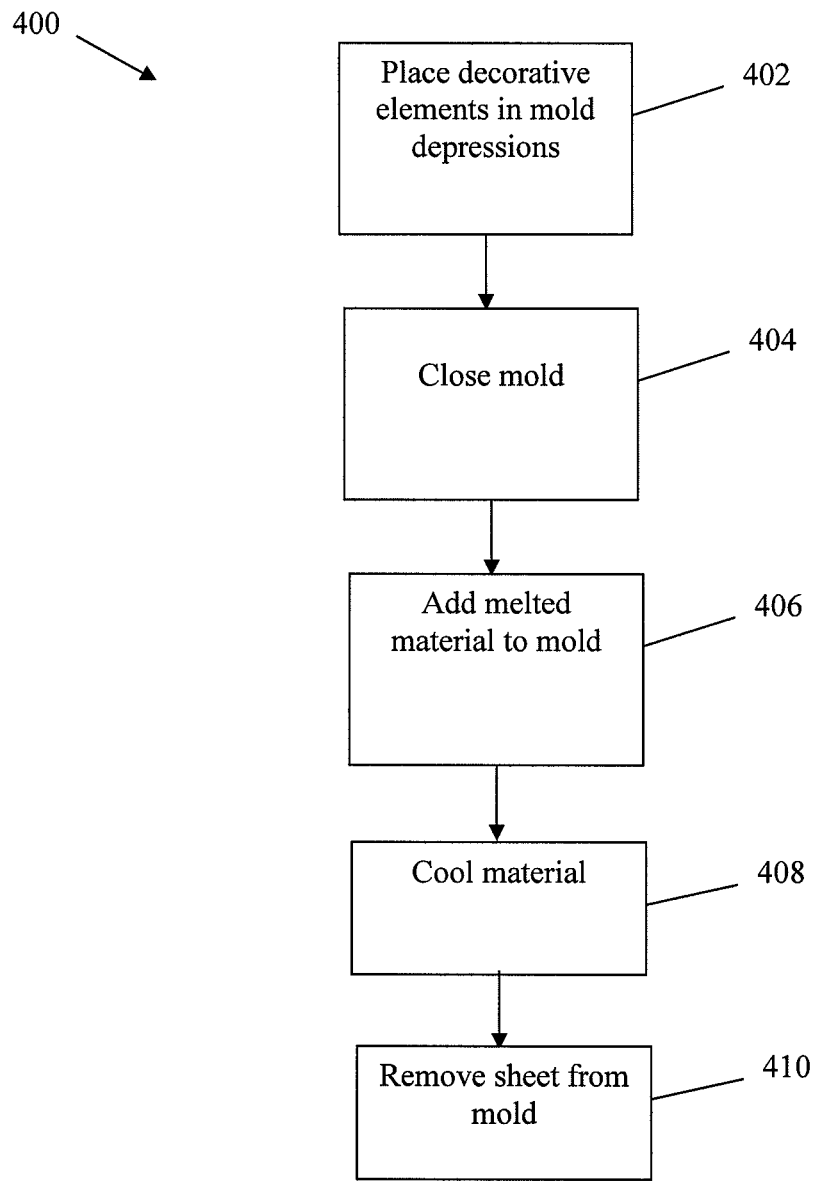
FIG. 4 is a flow chart for manufacturing a sheet of splint or cast material according to one embodiment of the invention.

As illustrated in FIG. 3, a split mold 300 may be used to manufacture a sheet of splint material, such as a sheet of low temperature thermoplastic. A first mold portion 302 includes depressions 306 for holding decorative elements, for example, rhinestones 102. The decorative elements are placed in depressions 306 (act 402) with the decorative surface of the decorative elements face down within the depressions 306. For ease of illustration, only one rhinestone 102 is shown in FIG. 3. However, a plurality of rhinestones and/or other decorative elements may be placed in each or any number of depressions to create a desired decorative pattern.

A second mold portion 304 is brought into contact with the first portion 302 (act 404) to close the mold and form a mold cavity. The portions of the decorative elements which protrude from the depressions 306 may be held in place by contact with an inner surface (not shown) of the second mold portion 304, or by contact with pins (not shown) or other elements which protrude from the second mold portion.

With the mold closed, melted low temperature thermoplastic is introduced to the mold cavity (act 406), for example by injection, and the thermoplastic material flows throughout the cavity to form the sheet. The thermoplastic flows around portions of the decorative elements which protrude from the depressions 306 such that when the material cools (act 408), the decorative elements are embedded in the fabricated sheet. The sheet is then removed from the mold (act 410), and the method may be repeated to form another sheet.

The decorative elements may be embedded in the sheet at a depth at which the decorative elements remain joined to the sheet of splint material when the sheet is heated and molded into a splint shape. In one illustrative embodiment, rhinestones may be embedded to a depth between 0.5 mm and 1 mm in a sheet that has a thickness of 1.5 mm. In some embodiments, the rhinestones may be embedded to a depth of 0.75 mm in a sheet that has a thickness of 1.5 mm. It is to be understood that sheets of larger or smaller thicknesses may be used, and decorative elements may be embedded to various depths within the sheets.

Various methods of forming a sheet of low temperature thermoplastic suitable for forming into a splint or cast may be used as would be apparent to one of ordinary skill in the art. Extrusion molding, injection molding, compression molding and matched-die molding are a few examples of methods of forming a low temperature thermoplastic sheet.

Figure 5:
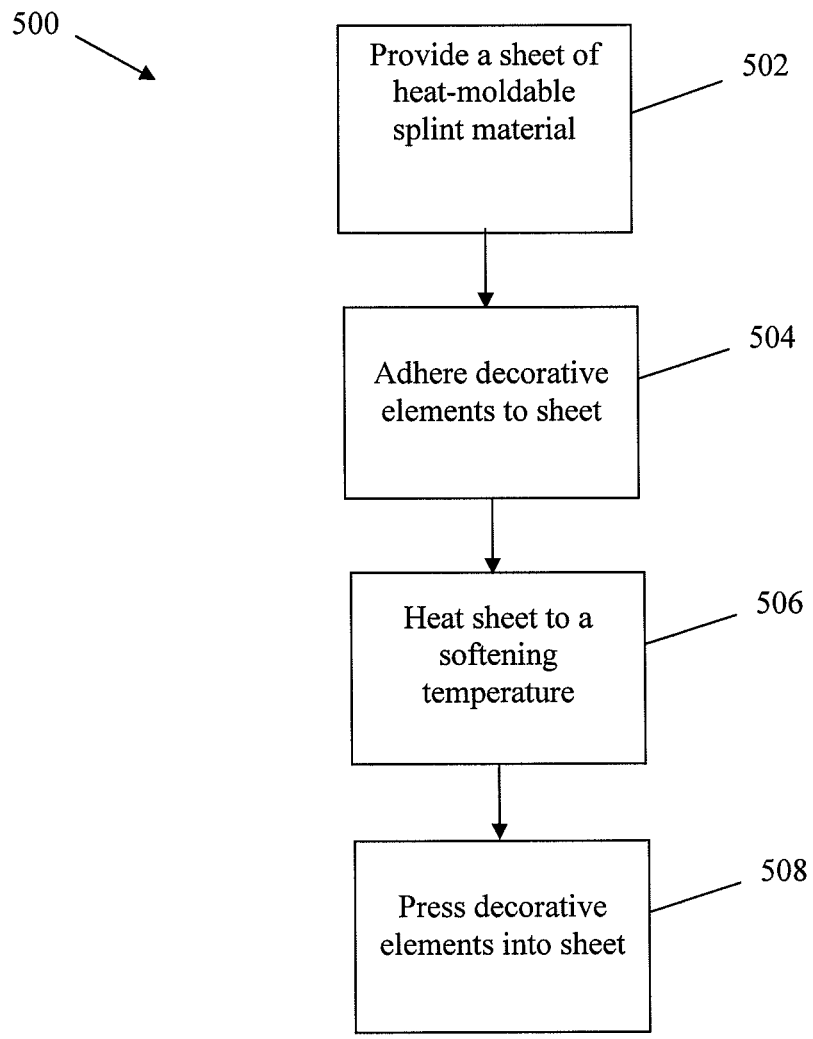
FIG. 5 is a flow chart for manufacturing a sheet of splint or cast material according to another embodiment of the invention.

In another illustrative embodiment shown in FIG. 5, a method 500 of manufacturing a sheet of splint material involves embedding decorative elements in a low temperature thermoplastic sheet after the sheet has been formed. The method includes providing (act 502) a sheet of splint material. In some embodiments, the sheet may have been previously fabricated. Decorative elements may be adhered to the sheet in desired positions (act 504) using heat-resistant and/or water-resistant adhesive. The sheet is heated to a temperature at which the low temperature thermoplastic softens (act 506), for example, above its melting point temperature). The decorative elements are pressed into the sheet (act 508) to a depth sufficient retain hold the decorative elements when the sheet is later heated for shaping on a patient. For example, the decorative elements may be pressed into the sheet such that a base of each decorative element penetrates to a depth of approximately 0.75 mm for a sheet thickness of approximately 1.5 mm.

According to some embodiments, if the decorative elements are not adhered to the sheet before heating of the sheet, an adhesive may be used simultaneously with pressing the decorative elements into the heated sheet. For example, the sheet may be heat-softened, and then a decorative element with adhesive on its bottom surface may be pressed into the sheet.

In some embodiments, the decorative elements may be embedded into the sheet of splint material by positioning the decorative elements on the sheet and pressing a block of planar material against the decorative elements. In other embodiments, the decorative elements may be pressed into the sheet by holding the decorative elements in a desired pattern on a plate and pressing a heated sheet of splint material against the decorative elements. The plate may be a flat plate with depressions or other components for holding the decorative elements in certain positions. The plate may be configured to hold decorative elements in a single pattern such that a single type of sheet of decorative elements may be repeatedly formed. Alternatively, the plate may have a grid pattern or other pattern of depressions to permit various designs to be formed by placing decorative elements in a selected subset of the depressions.

Figure 6:
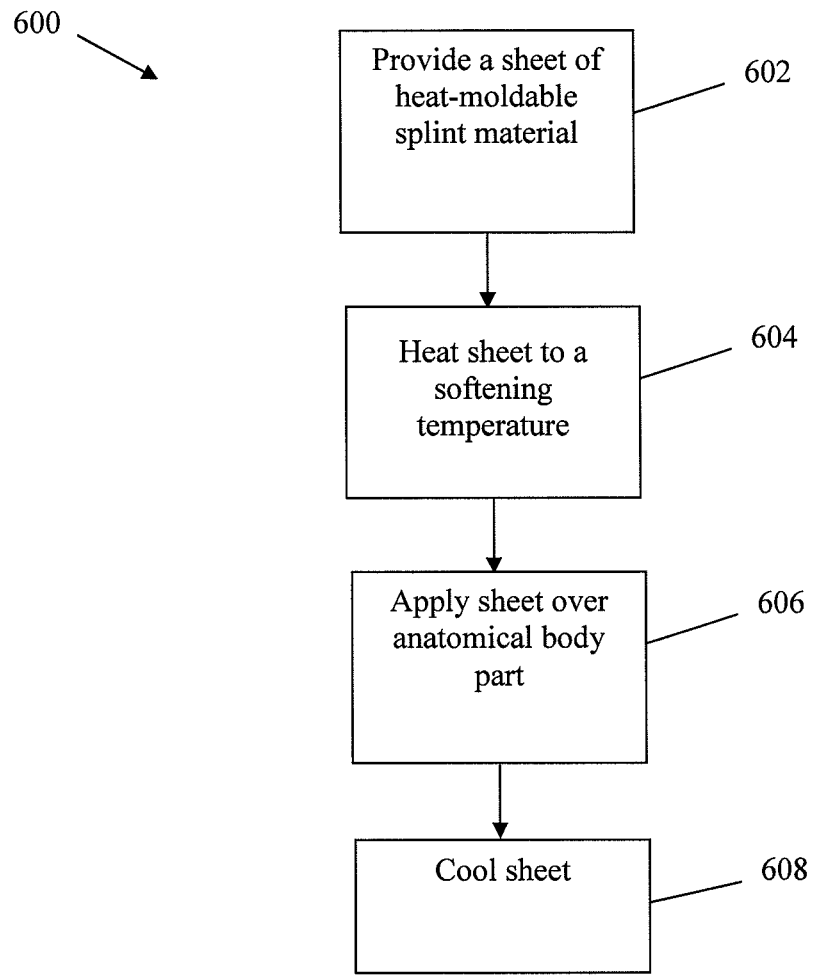
FIG. 6 is a flow chart for of applying a splint or cast to a patient according to one embodiment of the invention.

In one illustrative embodiment shown in FIG. 6, a method 600 of applying a splint to a patient may include providing a sheet of thermoplastic material (act 602) which has decorative elements that were previously integrated with the sheet. In some embodiments, a patient or doctor may select a sheet of splint material from among a number of color and or decorative options. Each sheet provides the same general immobilization and/or support functional properties.

The sheet is heated to a first, softening temperature (act 604), for example, its melting point temperature, so that the sheet becomes pliable. In some embodiments, heating is achieved by placing the sheet in heated or boiling water. In other embodiments, the sheet may be heated by placing the sheet against a heater plate, or within a heated enclosure. In some embodiments, the melting point temperature of the sheet may be between 50 degrees Celsius and 100 degrees Celsius inclusive. The melting point temperature may be between 62 degrees and 75 degrees Celsius inclusive in some embodiments. Once heated, the sheet may be allowed to cool to a temperature which is acceptable for application of the splint to the human body. For example, in some embodiments, a low temperature thermoplastic may be used which remains pliable for at least one minute when cooled to 45 degrees Celsius so that the sheet may be wrapped around or shaped over the subject body part (act 606). In some embodiments, the thermoplastic may remain pliable for several minutes at 45 degrees Celsius, and/or remain pliable at a lower temperature for a sufficient amount of time to permit shaping and applying the splint to the patient. In this regard, cooling of the material may occur both before and after application of the material to the patient because the material may take time to harden after cooling below the melting point temperature or other temperature.

The thermoplastic material may be self-bonding such that sections of heated material may be pressed against other sections of heated material, so that the sections may join and remain joined when the material hardens. In other embodiments, fastening elements such as zippers or hook-and-loop fasteners, for example, may be provided at or near edges of the sheet for attaching cooperating edges of the sheet to each other when applying the splint to a body part. A hand-held heat gun may be used to heat particular regions of a splint which require minor alterations.

In some embodiments, the sheet may be molded into a splint shape without shaping the sheet directly on the patient. For example, the sheet may be heated and then formed into a splint shape by pressing the sheet over a mold, or simply by molding the sheet with one's hands.

The molded splint may be cooled (act 608) to temperature at which the low temperature thermoplastic hardens. The cooling step may include simply exposing the splint to ambient temperatures of between 20 degrees Celsius and 25 degrees Celsius. For purposes herein, cooling refers to both passive cooling (e.g., exposing the splint material to ambient temperatures) and active cooling (e.g., applying cool water or air to the splint material). For purposes herein, as relating to thermoplastics or sheets of splint material, the term "harden" means bringing the material to a state where the material is resistant to a permanent shape change under typical handling forces. For example, a thermoplastic which is cooled for a sufficient amount of time below its melting point temperature cannot be shaped into a new shape that the material itself can retain (that is, unless the thermoplastic is first re-heated). A sheet of thermoplastic which is in a hardened state may be bendable, twistable flexible, etc., but the sheet will return to substantially the same shape after the external forces are removed.

Figure 7:
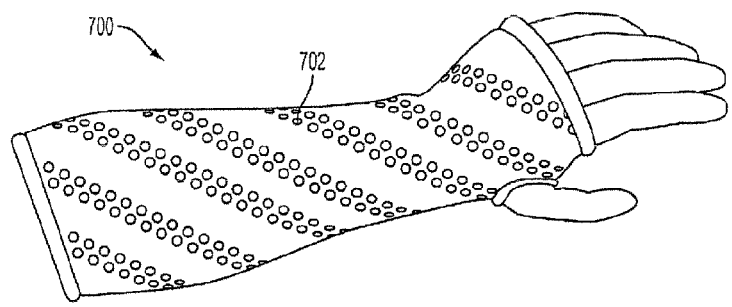
FIG. 7 shows splint material wrapped about a patient's wrist with the splint material including pre joined decorative elements according to one embodiment of the invention.

FIG. 7 shows a decorated splint 700 wrapped around a patient's wrist with integrated decorative elements 702 in a diagonal pattern. While embodiments disclosed herein may be used to integrate the decorative elements with the sheet of splint material before the splint is molded on the patient, additional decorative elements may be added to the splint after the splint has been applied to the patient for customization of the design. For example, after the splint hardens, additional decorative elements may be adhered to the splint.

In other embodiments, decorative elements may be pressed into the splint material after the splint material has been molded over the patient, but before the material completely hardens.

The thermoplastic sheets used for forming the splints disclosed herein may be provided in various colors, for example by including dyes within the heat-moldable material. In some embodiments, a sheet of splint material may have color added after the sheet of material has been manufactured, for example by painting the sheet.

Figure 8:
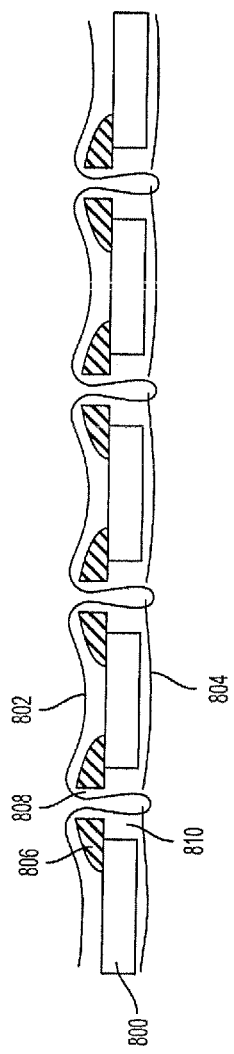
FIG. 8 is a side view of a sheet of splint or cast material with decorative elements joined to the sheet using an attachment element.

According to another embodiment of the invention, decorative elements may be integrated with a sheet of splint material by using an attachment element to join the decorative elements to the sheet. For example, as shown in FIG. 8, monofilament lines 802, 804 may be used to attach a bead 806 to a sheet 800 of low temperature thermoplastic. In the embodiment of FIG. 8, each bead 806 has a through-hole 808, and the sheet 800 has perforations 810. An industrial sewing machine may be used to interlace the two monofilament lines to join the beads 806 to the sheet 800.

After heating, the beads 806 may remain joined to sheet 800 only with monofilament lines 802, 804, or, in some embodiments, the beads 806 (or other decorative elements) may be pressed into sheet 800 when it is heated and becomes pliable. To press beads 806 into sheet 800, heated sheet 800 may be lay flat, and a solid planar block may be pressed onto the decorative elements. Other attachments elements, such as polyester thread or nylon, for example, may be used to join decorative elements to a sheet of splint material.

Figure 9A:
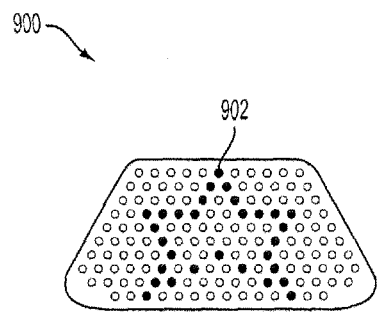
FIG. 9a is a top view of a sheet of splint or cast material including decorative elements according to one embodiment of the invention.
Figure 9B:
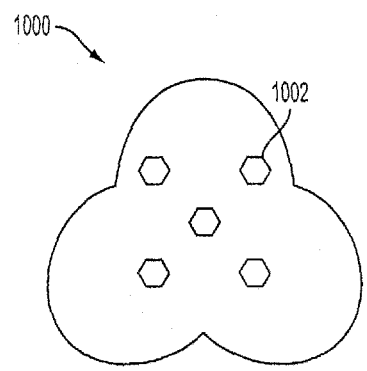
FIG. 9b is a top view of a sheet of splint or cast material including decorative elements according to another embodiment of the invention.
Figure 9C:
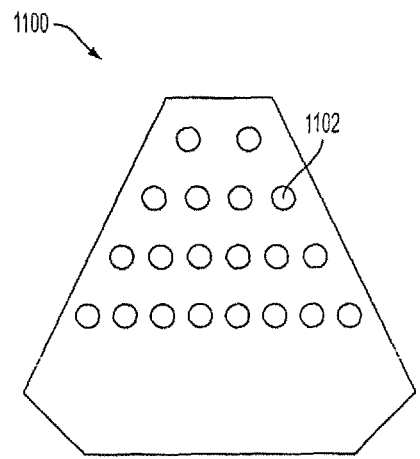
FIG. 9c is a top view of a sheet of splint or cast material including decorative elements according to yet another embodiment of the invention.
Figure 9D:
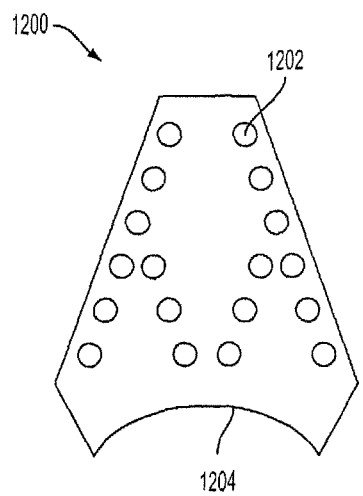
FIG. 9d is a top view of a sheet of splint or cast material including decorative elements according to a further embodiment of the invention.
Figure 10:
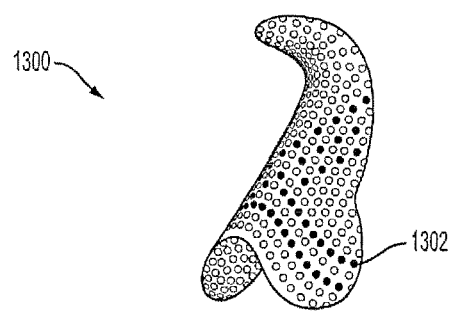
FIG. 10 is a perspective view of a molded nose splint including pre joined decorative elements according to a one embodiment of the invention.

As indicated above, a moldable, decorative sheet may be provided in various shapes. For example, a trapezoid-shaped sheet 900 is shown in FIG. 9a with beads 902 joined in a star design. Of course any other desired type of decorative element may be used. FIG. 9b shows a sheet 1000 which may be particularly suited for use as a nose splint and includes jewels 1002 integrated with the sheet. Sheet 1000 is shown without any perforations, though the sheet may include perforations if desired. FIG. 9c shows decorative elements 1102 integrated with a sheet 1100 which has been pre-cut to have a generally triangular shape with straight edges at each corner. A sheet 1200 including integrated decorative elements 1202 and a curved bottom edge 1204 is shown in FIG. 9d. A molded nose splint 1300 is illustrated in FIG. 10 with beads 1302 attached.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A moldable decorative splint material comprising:
a heat-moldable sheet of splint material adapted to become sufficiently pliable when heated to a first temperature to allow the sheet to be molded into a splint configuration that conforms to an anatomical body part and to become hard when cooled to a second temperature to retain the splint configuration; and
a plurality of decorative elements at least partially embedded in the sheet of splint material. the decorative elements comprising at least one of rhinestones, decorative beads, crystals, gemstones or jewels, and the decorative elements to be retained by the sheet of splint material when the sheet is heated to the first temperature, molded into a splint configuration, and cooled to the second temperature.

2. A moldable decorative splint material as in claim 1, wherein the decorative elements are embedded in the sheet of splint material such that no part of the decorative elements protrude above an upper surface of the splint material.

3. A moldable decorative splint material as in claim 1, wherein the sheet of splint material includes a plurality of perforations.

4. A moldable decorative splint material as in claim 3, wherein the decorative elements are positioned at locations of at least some of the perforations.

5. A moldable decorative splint material as in claim 1, wherein the decorative elements comprise rhinestones.

6. A moldable decorative splint material as in claim 1, wherein the decorative elements comprise decorative beads.

7. A moldable decorative splint material as in claim 1, wherein the splint material comprises a low temperature thermoplastic material.

8. A sheet of splint or cast material as in claim 7, wherein the low temperature thermoplastic material is poly epsilon caprolactone.

9. A moldable decorative splint material as in claim 1, wherein the splint material consists essentially of a low temperature thermoplastic material.

10. A method of fabricating a moldable decorative splint material, the method comprising acts of:
  (a) providing a heat-moldable splint material adapted to become sufficiently pliable when heated to a first temperature to allow the splint material to be molded into a splint configuration that conforms to an anatomical body part and to become hard when cooled to a second temperature to retain the splint configuration; and
  (b) at least partially embedding a plurality of decorative elements in the splint material, the decorative elements comprising at least one of rhinestones, decorative beads, crystals, gemstones or jewels, the decorative elements to be retained by splint material when the splint material is heated to the first temperature, molded into a splint configuration, and cooled to the second temperature.

11. A method as in claim 10, wherein:
  act (a) comprises forming a low temperature thermoplastic material into a sheet of splint material; and
  act (b) comprises embedding the decorative-elements in the low temperature thermoplastic material such that no part of the decorative elements protrudes above an upper surface of the splint material during act (a).

12. A method as in claim 10, wherein act (b) comprises heating the splint material and at least partially embedding the decorative-elements in the splint material by pressing the decorative elements into the splint material.

13. A method as in claim 10 wherein the material is formed as a sheet of heat-moldable splint material including a plurality of perforations.

14. A method as in claim 10, wherein act (b) comprises at least partially embedding rhinestones with the splint material.

15. A method as in claim 10, wherein act (b) further comprises integrating each of the decorative elements with the splint material using an attachment element.

16. A method as in claim 10, wherein the material is formed as a sheet of low temperature thermoplastic.

17. A method as in claim 16, wherein the low temperature thermoplastic is poly epsilon caprolactone.

18. A method of applying a splint to a patient, the method comprising acts of:
  (a) heating a sheet of splint material to a first temperature at which the splint material becomes sufficiently pliable to allow the sheet to be molded into a splint configuration that conforms to an anatomical body part, the splint material being at least partially embedded with a plurality of decorative elements that remain at least partially embedded with the splint material during heating, wherein the decorative elements comprise at least one of rhinestones, decorative beads, crystals, gemstones or jewels;
  (b) molding the sheet of splint material over the anatomical body part and into the splint configuration; and
  (c) cooling the sheet of splint material until the splint material hardens to retain the splint configuration.

19. A method of applying a splint to a patient as in claim 18, wherein the plurality of decorative elements comprises rhinestones.

20. A method of applying a cast or splint to a patient as in claim 18, wherein the splint material comprises a low temperature thermoplastic.

21. A moldable decorative splint material comprising:
  a heat-moldable sheet of splint material adapted to become sufficiently pliable when heated to a first temperature to allow the sheet to be molded into a splint configuration that conforms to an anatomical body part and to become hard when cooled to a second temperature to retain the splint configuration; and
  a plurality of decorative elements at least partially embedded in the sheet of splint material, the decorative elements being discrete from one another, and the decorative elements to be retained by the sheet of splint material when the sheet is heated to the first temperature, molded into a splint configuration, and cooled to the second temperature.

* * * * *

UNITED STATES PATENT AND TRADEMARK OFFICE
CERTIFICATE OF CORRECTION

| | | |
|---|---|---|
| PATENT NO. | : 8,545,422 B2 | Page 1 of 1 |
| APPLICATION NO. | : 13/021169 | |
| DATED | : October 1, 2013 | |
| INVENTOR(S) | : Cristina Watson | |

It is certified that error appears in the above-identified patent and that said Letters Patent is hereby corrected as shown below:

In the Claims:

In claim 1, at column 8, line 64, delete "." and insert --,--;

In claim 11, at column 9, line 46, delete "-";

In claim 12, at column 10, line 1, delete "-";

In claim 18, at column 10, line 25, delete ":" and insert --;--.

Signed and Sealed this
Tenth Day of December, 2013

Margaret A. Focarino
*Commissioner for Patents of the United States Patent and Trademark Office*